United States Patent [19]

Kea et al.

[11] Patent Number: 4,710,567
[45] Date of Patent: * Dec. 1, 1987

[54] SEPARATION AND PURIFICATION OF SUGAR ESTERS SYNTHESIZED FROM BOTH AQUEOUS AND NONAQUEOUS SYSTEMS

[75] Inventors: Sandra Kea; Charles E. Walker, both of Lincoln, Nebr.

[73] Assignee: Nebraska Department of Economic Development, State of Nebraska, Lincoln, Nebr.

[*] Notice: The portion of the term of this patent subsequent to Jul. 28, 2004 has been disclaimed.

[21] Appl. No.: 741,229

[22] Filed: Jun. 4, 1985

Related U.S. Application Data

[63] Continuation-in-part of Ser. No. 639,783, Aug. 10, 1984.

[51] Int. Cl.$^4$ .............................................. C07H 1/00
[52] U.S. Cl. ................................... 536/119; 536/115; 536/127
[58] Field of Search .................... 536/119, 18.2, 115

[56] References Cited

U.S. PATENT DOCUMENTS

| | | | |
|---|---|---|---|
| 1,959,590 | 5/1934 | Lorand | 536/119 |
| 2,759,922 | 8/1956 | Gibbons | 536/18.2 |
| 2,948,716 | 8/1960 | Davis | 536/119 |
| 2,948,717 | 8/1960 | Babayan et al. | 536/119 |
| 3,249,600 | 5/1966 | Nobile et al. | 536/119 |
| 3,378,543 | 4/1968 | O'Boyle | 536/119 |
| 3,378,544 | 4/1968 | O'Boyle | 536/119 |
| 3,384,634 | 5/1968 | O'Boyle | 536/119 |
| 3,714,144 | 1/1973 | Feuge et al. | 536/119 |
| 3,748,324 | 7/1973 | Mizutani et al. | 536/119 |
| 3,956,278 | 5/1976 | Prey | 536/119 |

FOREIGN PATENT DOCUMENTS

| | | | |
|---|---|---|---|
| 826801 | 1/1960 | United Kingdom | 536/115 |
| 890136 | 2/1962 | United Kingdom | 536/115 |
| 1045182 | 10/1966 | United Kingdom | 536/115 |

OTHER PUBLICATIONS

Vogel's "Practical Organic Chemistry", 4th Ed., Longman, 1978, pp. 456-457.
Rizzi et al., "Jour. of the American Oil Chemists' Society", vol. 55, pp. 398-401, 1978.
Parker et al., from "Sucrochemistry", 'ACS Symposium Series 41', pp. 97-114, 1977.
James et al., "American Chemical Society", Carb 73, p. 172, 1976.
Weiss et al., reprint from the "Jour. of the American Oil Chemists' Society", vol. 48, No. 4, pp. 145-148, 1971.
Zeringue et al., reprint from the "Jour. of the American Oil Chemists' Society", vol. 53, No. 12, pp. 719-721, 1976.
Zeringue et al., reprint from the "Jour. of the American Oil Chemists' Society", vol. 53, No. 9, pp. 567-571, 1976.
Weiss et al., reprint from the "Jour. of the American Oil Chemists' Society", vol. 49, No. 9, pp. 524-526, 1972.
Feuge et al., Jour. of the American Oil Chemists' Society, vol. 47, pp. 56-60, 1970.

*Primary Examiner*—Johnnie R. Brown
*Attorney, Agent, or Firm*—Lucas & Just

[57] ABSTRACT

Sugar esters are separated and purified by forming an aqueous mixture containing salt from which water is distilled off to remove unreacted volatile material from the raw sugar esters. Thereafter an organic extraction solvent is mixed into the aqueous mixture which upon standing separates into a plurality of layers containing sugar esters of different degrees of substitution which are recovered from the separated layers. The separated sugar esters may be further refined by mixing with water and by freeze drying the aqueous mixture.

31 Claims, 4 Drawing Figures

SEPARATION AND PURIFICATION OF SUGAR ESTERS SYNTHESIZED FROM BOTH AQUEOUS AND NONAQUEOUS SYSTEMS

This application is a continuation-in-part of copending application Ser. No. 639,783 filed Aug. 10, 1984.

This invention is directed to a controlled process for purifying sugar esters to provide edible sugar esters for use in food products for human consumption and a high purity of sugar esters for use in surfactants.

Sugar esters have been produced by synthesizing sucrose with fatty acids having from 12 to about 22 carbon atoms in an aqueous reaction system as described in U.S. Pat. No. 3,644,333. Suggestions have been made to produce sucrose sugar esters in aqueous media by reaction with an organic acid chloride such as palmitoyl chloride as described in U.S. Pat. No. 2,948,717.

These prior art processes have the drawback of hydrolysis that occurs in aqueous media when the selected interesterification reagent is an organic acid chloride which converts back to acid form and thereby becomes ineffective for producing sugar esters. Aqueous systems for producing sugar esters also require care to prepare a transparent micro-emulsion in order to obtain the high yields required for commercial operations. Moreover as described in U.S. Pat. No. 3,748,324, purification of the sugar ester product is difficult to achieve and frequently involves the use of toxic materials which only complicate and add to the expense of producing a non-toxic edible sugar ester for use in food products for human consumption.

It has recently been discovered that sugar esters can be produced using a substantially anhydrous liquid system which overcomes the problems of the aqueous systems of the prior art. This is accomplished in accordance with application Ser. No. 639,783 filed July 10, 1984, wherein a selected sugar is reacted under substantially anhydrous conditions with an organic acid chloride having from 2 to 22 and more carbon atoms at a temperature that may range from about ordinary room temperature up to about 250° C. and more. Best results are achieved by vigorously mixing the reactants and by using a dry inert gas purge to strip out moisture and establish truly anhydrous liquid conditions for the synthesis reaction. A liquid solvent is preferably used for ease of reaction and a catalyst is of advantage for better synthesis and high yields.

The present invention is directed to separating and purifying sugar esters synthesized in either a nonaqueous system such as the one disclosed in U.S. patent application Ser. No. 639,783 or an aqueous system such as the ones disclosed in U.S. Pat. Nos. 3,644,333 and 2,948,717. Best results are achieved where the sugar ester is synthesized in a substantially anhydrous system. These sugar esters are particularly advantageous for use as an ingredient in food products for human consumption. The present invention is also particularly advantageous for use with sugar esters made from sugars which are selected from the group of starch hydrolyzate sugars such as glucose (dextrose), maltose, maltotriose, etc., provided in an anhydrous system.

In accordance with the present invention, sugar esters are purified by mixing the crude sugar esters synthesized in any known manner with salt or a salt solution; adding an organic extraction solvent; mixing in an organic extraction solvent and then separating the sugar esters.

One of the novel aspects of the present invention is that room temperature and pressure can be maintained throughout the purification process.

Another novel aspect of the present invention is that the process does not affect the pH of sugar esters. Thus, the pH of the starting raw sugar ester is substantially the same as the purified sugar ester.

Yet another novel aspect of the present invention is that the purification process of the present invention works on sugar esters synthesized in any manner.

Still another novel aspect of the present invention is that upon mixing the organic extraction solvent into the aqueous mixture and allowing the mixture to stand at room temperature and pressure, the mixture separates into three layers. These three layers are truly surprising and totally unexpected. It has been found that the middle layer is an emulsion of water, organic extraction solvent and sugar esters and yields the sugar esters with the best emulsifying capabilities and the best for use in food. It has also been discovered quite unexpectedly that the top layer of this three-layer system yields sugar esters with the highest degree of substitution while the lower layer produces sugar esters with the lowest degree of substitution and the middle layer produces sugar esters with an intermediate degree of substitution. In this manner, sugar esters with different degrees of substitution are separated by the present process. Thus, the present process also works as a process for separating sugar esters with different degrees of substitution. It should be readily apparent that this separation aspect of the present invention could be used on already purified sugar esters to divide the sugar esters into three different groups depending on the degree of substitution of the sugar esters. In this respect, the present process would be used merely to separate and not to purify.

Sugar esters made in accordance with the anhydrous method described above have such excellent emulsifying characteristics that purification by the classic liquid-liquid extraction processes is difficult and satisfactory yields are not obtained as a practical matter. This drawback has now been overcome and excellent yields of purified edible sugar esters are achieved by separating and extracting the sugar esters in accordance with the present invention.

The process of separation and purification works on raw sugar esters from any synthesis process. For example, in U.S. Pat. No. 2,948,717, Example 1 therein, the thick paste containing the crude sugar ester is suitable for separation and purification by the present process.

With respect to U.S. Pat. No. 3,644,333 which is incorporated herein by reference, the raw sugar esters produced from the synthesis process are suitable for separation and purification by the present process. Briefly, the '333 process entails combining a sugar in water with a fatty acid with a suitable emulsifying agent to form a transparent emulsion, removing virtually all the water and heating the composition under alkaline conditions to a temperature between about 60° C. to 200° C. to form the crude sugar esters.

In accordance with a preferred embodiment of the present invention, the reaction mixture containing raw starch hydrolyzate sugar esters remaining after the anhydrous liquid synthesis reaction is heated preferably under reduced pressure of about 725 mm of Hg vacuum to distill off as much as possible of the solvent remaining in the reaction mixture. The anhydrous raw sugar esters are then mixed with an aqueous solution of salt such as sodium chloride. Water is distilled off to remove the remaining solvent used in the synthesis reaction. For best results, after the distillation additional steps of adding and distilling off of water are repeated three or four times to remove as much of the synthesis reaction solvent as possible. An aqueous mixture containing the raw sugar esters is formed by adding water if necessary after distillation and the mixture is cooled to room temperature.

The distillation of water to remove solvent is carried out at low temperature preferably under vacuum to avoid burning or caramelization of sugar which would result in sugar esters of poor quality and color. If desired, water may be added to the raw sugar esters to provide an aqueous mixture for initial distillation followed by the addition and distilling off of water from the aqueous mixture formed by adding the salt solution. This step of mixing the raw sugar esters with the aqueous salt solution is important to facilitate separation and purification of the sugar esters.

It will be understood by those of skill in the art that when the sugar ester is synthesized in an aqueous system, the removal of a solvent will not be necessary. However, often there is a reason, such as an impurity of methanol in the sugar esters synthesized in an aqueous system, which would make it advantageous to carry out a distillation step. In such a case, distillation in the above described manner can be employed.

Except for the distillation of water to remove the solvent, which is optional with respect to raw sugar esters synthesized in an aqueous system, the purification process of the present invention for sugar esters synthesized in both aqueous and nonaqueous systems is identical.

After the addition of salt and the optional distillation step, the aqueous mixture of raw sugar esters at room temperature is transferred to any conventional separation equipment such as a separatory funnel for separation and extraction of the sugar esters.

The next steps in the purification process are the addition and mixing of organic extraction solvent. Acceptable organic extraction solvents are ethers. The ether is added and mixed into the aqueous mixture which upon standing at room temperature separates into a plurality of layers. The majority of the ether with dissolved sugar esters and unreacted fatty acid forms a top layer. The second middle layer is an emulsion containing water, ether and sugar esters and the third bottom layer contains mostly water, sugar esters and unreacted sugars. The majority of salt is contained in this lower layer. Continuous ether extraction may be used to extract the sugar esters from the bottom water layer. The sugar esters are recovered by distilling off the ether which is condensed and may be reused in the separation and extraction process.

It has been determined that the top ether layer contains sugar esters with the highest degree of substitutions from the synthesis reaction while the middle layer contains sugar esters with a medium degree of substitutions and sugar esters with the lowest degree of substitutions or the shortest chain length are recovered from the bottom water layer. This is of advantage for separating the sugar esters having different substitution characteristics which provide different functional characteristics for use as ingredients in different food products.

As is known, sugar esters are used in a wide variety of food products such as baked goods, beverages, spices, soups, coffee whiteners, dairy products, desserts and meat products; and in the cosmetic industry for soaps, lotions, creams and the like. The sugar esters serve as emulsifying, improving, bodying and bulking agents and are used for encapsulating pharmaceutical and other products such as essential flavoring oils. Sugar esters are also used in the manufacture of detergent.

Another advantage of the process of the present invention is the high yield of starch hydrolyzate sugar ester obtained by separation and purification which may range up to 90% and more of the available product in the starting mixture in sugar esters synthesized from an anhydrous system.

A preferred detailed embodiment of the present invention for separation and purification of sugar esters is illustrated in the drawing in which.

Figure 1:
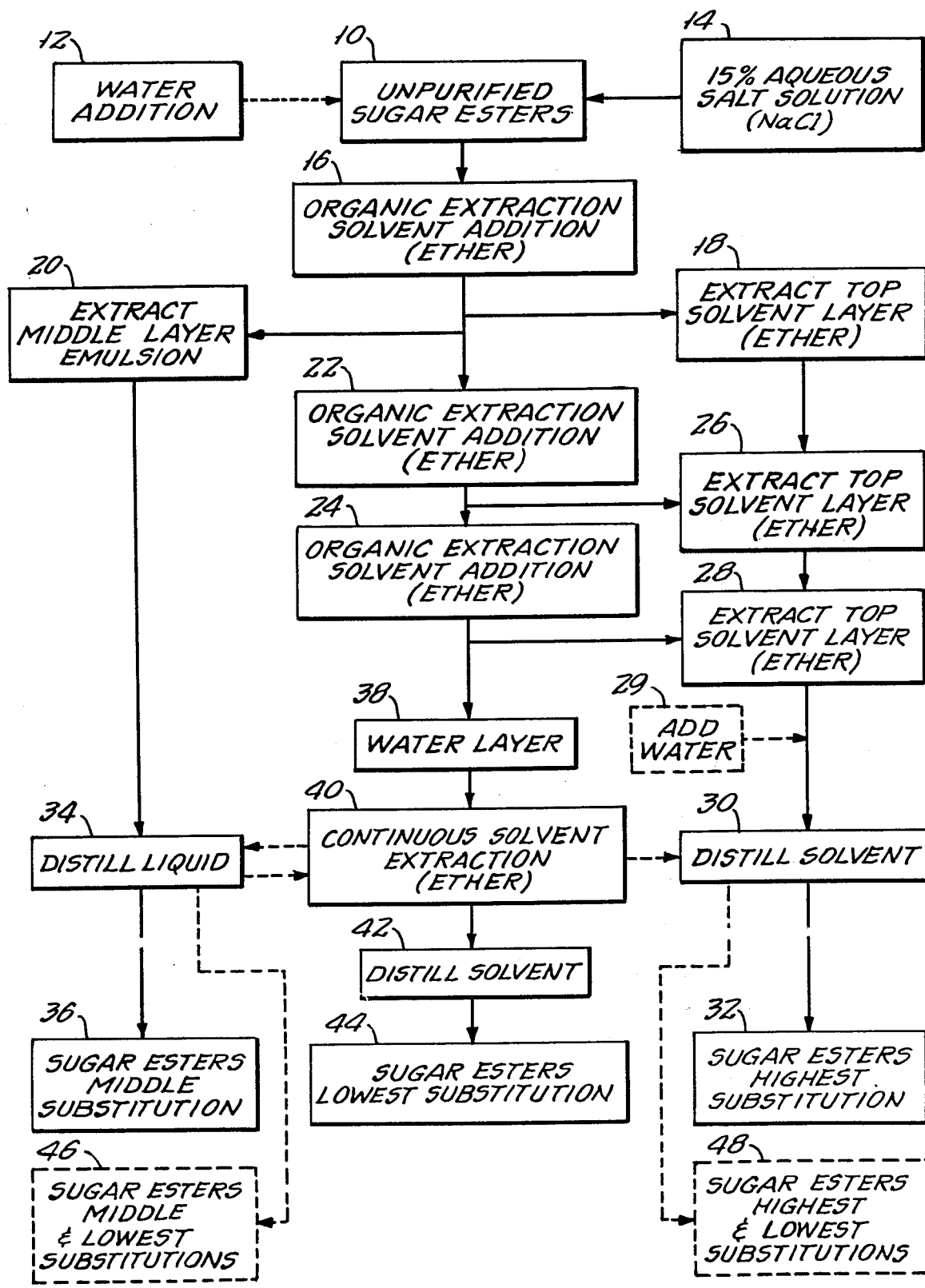
FIG. 1 is a schematic illustration of the steps in this preferred embodiment of the process of the present invention.

Referring to FIG. 1, 10 is a conventional vessel in which an aqueous mixture is formed containing from about 5.0% by weight to about 80% by weight of the raw unpurified sugar esters and preferably from about 10% to about 20% by weight of raw sugar esters. If the sugar ester is already contained in an aqueous mixture, the amount of water already in the system should be taken into account for these calculations. Preferably non-toxic ingredients are used to produce a food grade sugar ester.

The raw sugar ester from the anhydrous synthesis reaction is usually mixed with fatty acids, solvents and sugar. The volatile materials are preferably removed as much as possible by distillation preferably under vacuum to avoid caramelization of sugar which would result in a poor quality product with dark color. Water as indicated at 12 may be added to assist in distilling off volatile materials.

A non-toxic salt is added to the aqueous mixture prior to separation and purification of the sugar esters. The salt is an electrolyte that assists in separating the water and organic solvent extraction phases. Suitable non-toxic salts that may be used include sodium chloride, ammonium sulphate and calcium chloride.

The amount of salt used will vary but in general from about 1.0% by weight to about 50% by weight based on the weight of water may be employed. One convenient way to add the salt is to mix the raw sugar esters with a 15% by weight sodium chloride soluti on as indicated at 14 in FIG. 1. If the salt solution is used to form the aqueous mixture, the amount of salt solution employed is adequate to suspend the raw sugar esters therein.

When water is distilled off from the aqueous salt solution mixture in order to strip out undesirable materials from the synthesis reaction mass, the additional steps of the addition and distillation of water are preferably repeated two or three times to strip out as much of the undesirable materials as possible.

After the distillation step is finished, water is added if necessary to form an aqueous mixture which is cooled to about room temperature at normal atmospheric pressure.

An organic extraction solvent that does not react with the starch hydrolyzate sugar esters and in which the sugar esters will dissolve, become suspended or be colloidally dispersed is employed for separation and extraction of the sugar esters from the aqueous solution. It has been found that diethyl ether is an excellent solvent since the starch hydrolyzate sugar esters readily dissolve in the ether and its low boiling point of about 34.5° C. is ideal for distilling off the ether to recover the purified sugar esters. Other organic extraction solvents that may be used in accordance with the present invention include ethyl acetate and acetone.

The term organic extraction solvent used in the description and claims means those organic liquids that do not react with the starch hydrolyzate sugar esters and in which the sugar esters will dissolve, become suspended or colloidally dispersed.

The amount of organic extraction solvent employed may be varied over a wide range, but in general from about 4000% by weight to about 6000% by weight based on the weight of the raw sugar ester mixture will be adequate to keep distillation cost at a reasonable level.

In this preferred embodiment of the invention a plurality of ether extraction steps are used preferably at about ordinary room temperature and pressure. In the first step, the ether is mixed with the aqueous mixture of sugar esters at 16 in conventional separation apparatus. Upon standing the mixture separates into three portions. The portions are separated, as by pouring off the top portion to remove it at 18 and by removing the middle portion at 20. The remaining bottom portion, which contains a high amount of the water, is again treated to a second ether extraction at 22 and to a third ether extraction at 24. In each of these extraction steps the top portion is removed at 26 and 28 and combined with the top portion removed at 18.

The top portions of the mixture removed at 18, 26 and 28 have a high extraction solvent content and contain sugar esters with the highest degree of substitutions. These are recovered at 32 as the residue obtained by distilling off the extraction solvent at 30. An optional step of adding water at 29 to the top portion at 28 prior to the distillation of the extraction solvent is preferred. The water is removed after step 30 by drying the aqueous sugar esters. The middle portion removed at 20 contains sugar esters in a middle range of substitutions which are recovered at 36 by distilling off the liquid emulsion of ether and water at 34. The bottom water portion 38 is subjected to continuous extraction at 40 in conventional manner as by passing ether up through the water layer and continuously removing the ether until there are virtually no sugar esters remaining in the water. The ether from 40 is accumulated at 42 and distilled off to recover the sugar esters at 44 which have the lowest degree of substitutions or lowest chain length. In all cases, distillation is carried out below the temperature at which the sugar ester would burn and caramelize using vacuum if necessary.

Various modifications may be used in accordance with the present invention. For example, the extraction solvent containing sugar esters with the lowest degree of substitution may be taken from 40 and combined with the middle portion for distillation at 34 in which case the sugar esters recovered at 46 will be a mixture of the lowest and middle range of substitutions. Alternatively, the extraction solvent from 40 may be combined with the top portions of extraction solvent at 30 in order to recover a mixture of sugar esters containing the highest and lowest degree of substitution at 48. The flexibility of separating and purifying sugar esters in accordance with the present invention to obtain a sugar ester product of different degrees of substitution is of particular advantage for producing sugar esters tailor made for use in a particular food product. In those cases where it is not important to separately recover esters having different degrees of substitution, continuous extraction of the aqueous mixture may be used at 16 as by passing the extraction solvent up through the aqueous mixture continuously to strip out the sugar esters which are recovered by accumulating the extraction solvent and distilling it off to recover the sugar esters without going through the plurality of separate extraction steps of 18 through 48.

In another embodiment of the present invention, the sugar esters recovered from the system of FIG. 1 may be further refined by mixing with water, and the resulting aqueous mixture is dried in any conventional manner. Suitable methods of drying include spray drying and freeze drying. The resulting sugar esters are particulate and in the form of a finely divided powder with light color.

Figure 3:
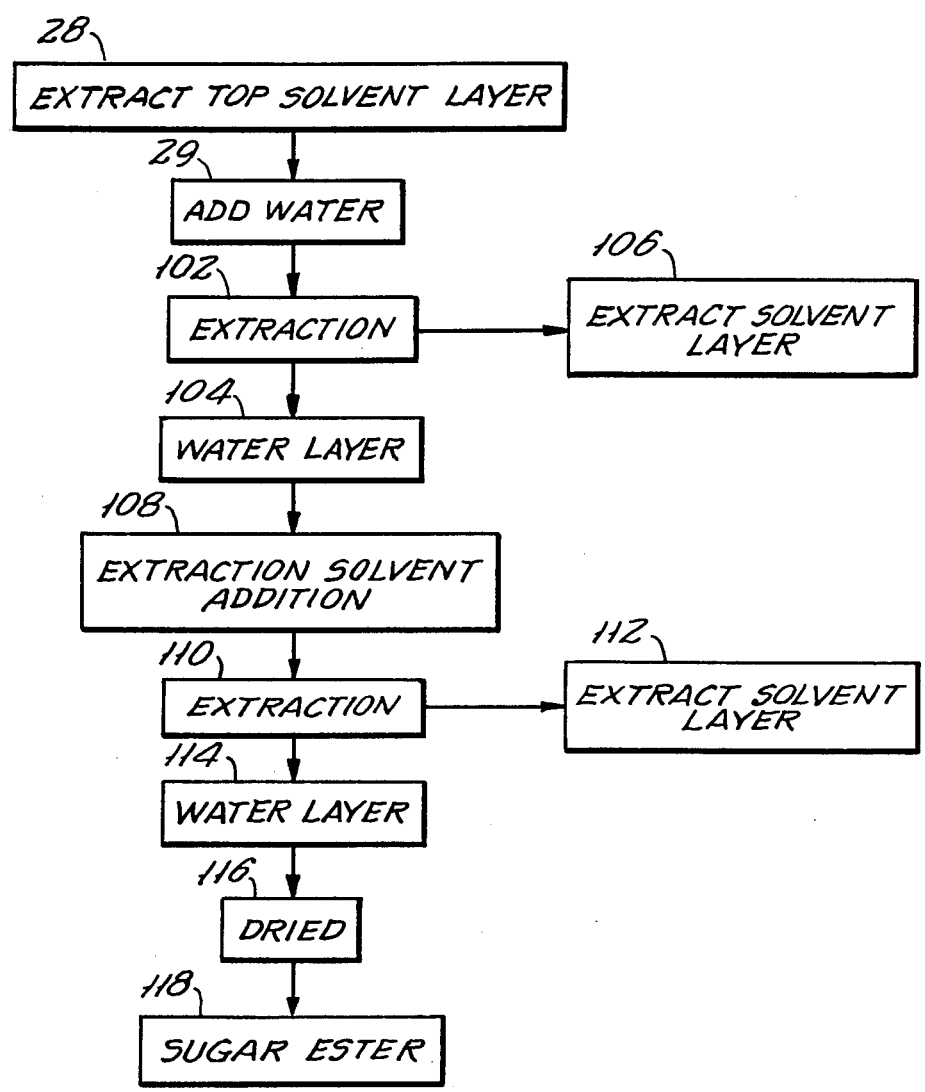
FIG. 3 is yet another schematic illustration of alternative steps to perform instead of the distillation performed on the top layer as shown in FIG. 1.

In an alternative embodiment, FIG. 3, instead of performing the distillation step at 30, after the water is added at 29 to the top layer 28, the aqueous extraction solvent solution is transferred to conventional extraction apparatus 102 and the water layer is distilled off at 104. The remaining extraction solvent layer (106) can either be discarded or further processed to extract any remaining sugar esters in the extraction solvent layer. Extraction solvent is added (108) and the extraction step performed (110) to remove the water layer (114). The extraction solvent layer (112) can again be further processed to remove any sugar esters which may be present in this layer. This addition of extraction solvent and extraction of the water layer is preferably performed two or three times. The final water layer is dried in any known conventional manner (116) to obtain dried sugar esters (118).

Figure 4:
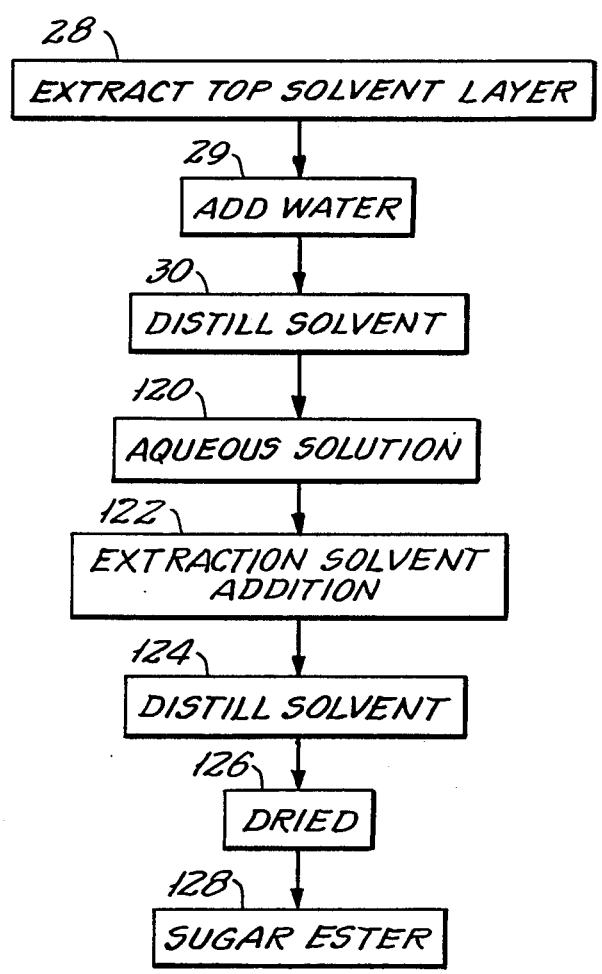
FIG. 4 is still another schematic illustration of an alternative to the distillation performed on the top layer as shown in FIG. 1.

In still another alternative embodiment, FIG. 4, water is added at 29 to the top layer 28 prior to performing the distillation at 30. After the distillation, more extraction solvent (122) is added to the remaining aqueous solution (120) and the distillation step repeated (124). This repetition is preferably performed two or three times. The aqueous solution is then dried (126) and a sugar ester obtained (128).

Figure 2:
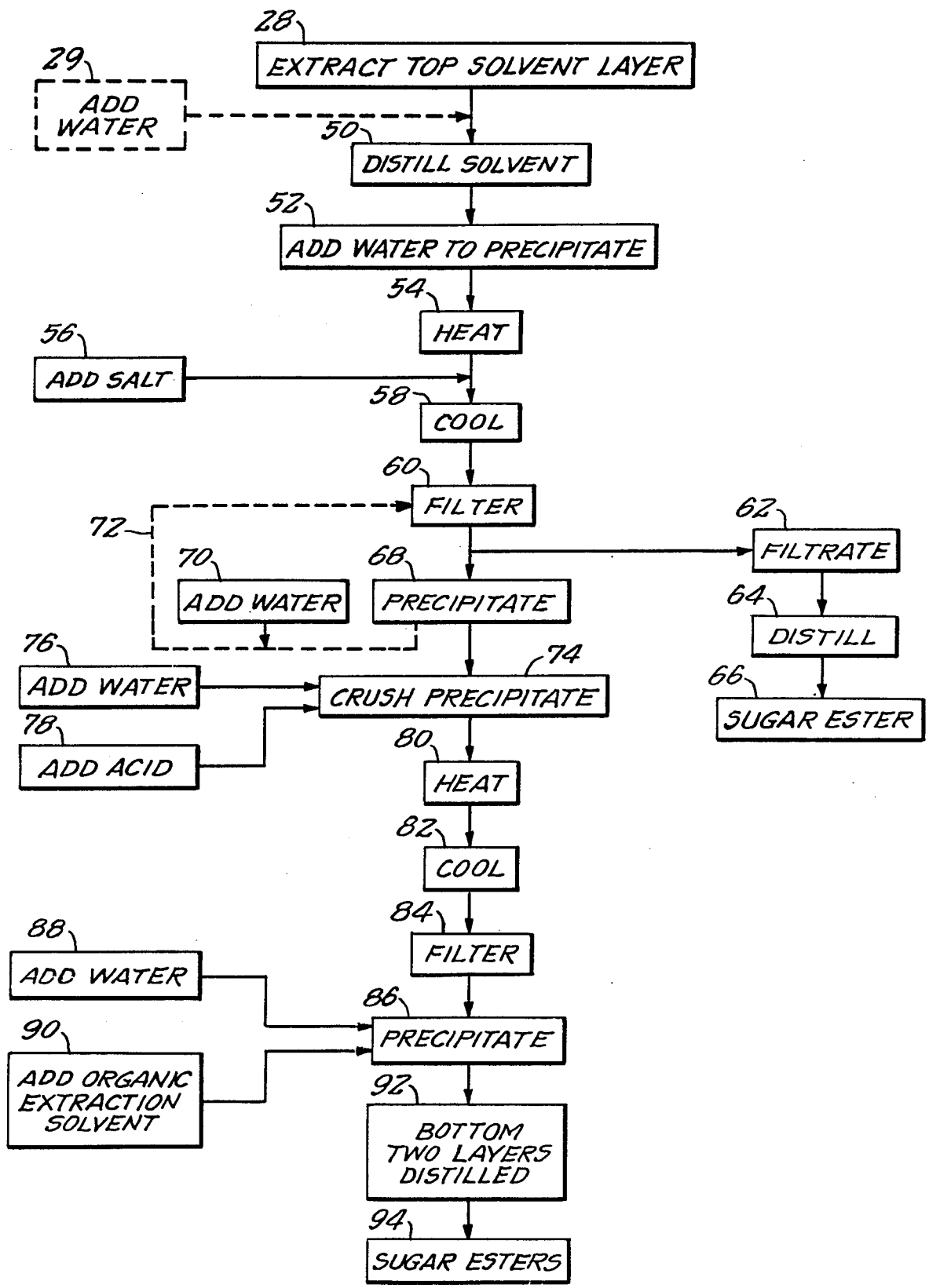
FIG. 2 is a schematic illustration of the steps performed in alternative to the distillation performed on the top layer as shown in FIG. 1.

In yet another embodiment of the present invention, FIG. 2, the extracted top layer is purified to a further extent to increase the yield of the sugar esters. This further purification is accomplished by taking the top layer 28 and distilling off the solvent 50. Then water is added to the precipitate 52. About 50 ml of water is added for about every 5 to 10 grams of precipitated material obtained from step 30. An optional step is to add water (29) to the top layer (28) prior to the distillation step (50). If this optional step is performed, after the distillation of the extraction solvent an aqueous solution remains and the addition of water at 52 is not needed.

This mixture is then heated (54) and a salt is added (56). Then the mixture is allowed to cool (58). During the heating and cooling steps, the mixture is subjected to constant stirring. Preferably, the mixture is heated to between about 70° C. to about 125° C. and more preferably to between about 80° C. to about 100° C. The amount of salt added depends on the fatty acid used to make the sugar ester. Acceptable salts include sodium chloride, potassium chloride and calcium carbonate. Calcium carbonate is preferred. Calcium carbonate is added on a 1:1 molar ratio to the theoretical number of moles of unreacted fatty acid present in the material obtained after step 30. In order to calculate the amount of salt needed, the assumption is made that all the material obtained from the distillation step 30 is unreacted fatty acid. Thus, the weight of material obtained from step 30 is divided by the molecular weight of the unreacted fatty acid used to synthesize the raw sugar ester. Preferably, the mixture is cooled to between about 15° C. to about 30° C. and most preferably to room temperature.

This mixture is then filtered (60). The filtrate (62) contains sugar esters and is distilled (64) to obtain the sugar esters (66). The precipitate (18) from this first filtration can then be remixed with water (70) and refiltered (72) a number of times, preferably 2 to 4. The amount of water used with the precipitate is about 50 ml of water per about 5-10 grams of precipitate. Each filtrate from these refilterings is saved because it contains sugar esters, and the filtrate is distilled to obtain the sugar esters, steps 62-66.

The final precipitate is crushed (74) and mixed with water (76) such that there are about 5 to 10 grams of precipitate for every 100 ml of water.

The redissolved precipitate is then mixed with an acid (78). The amount of acid added is equal to or greater than an equimolar amount of theoretical unreacted fatty acid present in the crushed precipitate. Any acid is acceptable; mineral acids are preferred. Acceptable mineral acids include phosphoric, hydrochloric or sulfuric; preferably, hydrochloric is used. The theoretical number of moles of unreacted fatty acid present in the crushed precipitate is determined by assuming that all of the crushed precipitate is unreacted fatty acid. Thus, the weight of the crushed precipitate is divided by the molecular weight of the fatty acid used to synthesize the sugar ester.

This mixture is then heated (80) and allowed to cool (82). During both the heating and cooling steps, the mixture is subject to constant stirring. The mixture is preferably heated to between about 70° C. to about 125° C. and more preferably to between about 80° C. to about 100° C. Preferably, the mixture is cooled to between about 15° C. to about 30° C. and more preferably to about room temperature. Once the mixture has cooled, it is filtered (84). The filtrate contains mainly salts and is not used.

The precipitate (86) from filtration (84) is then mixed with water (88) and organic extraction solvent (90). This mixture forms three layers. The two bottom layers contain the most sugar esters and are therefore retained while the top layer contains a very small amount of sugar esters. The two bottom layers are distilled (92) to obtain the sugar esters (94).

In accordance with the invention described in application Ser. No. 639,783, the sugar esters are synthesized in a substantially anhydrous liquid system. For best results, the selected sugar is a saccharide or mixture of saccharides produced by hydrolysis of starch with acid or enzymes in known manner from any variety of the edible starches. The starch hydrolyzate sugar may be the monosaccharide, glucose (dextrose), the disaccharide, maltose, the trisaccharide, maltotriose, etc. on up to the very long chain dextrins and mixtures thereof. Starch hydrolyzate mixed saccharides are customarily sold as ingredients for food products. These mixed starch hydrolyzate saccharides are classified by DE, which is the dextrose equivalent value, rated on a scale of 0 to 100. In accordance with the present invention, the selected starch hydrolyzate saccharide may be pure dextrose or maltose, etc. or a mixture of hydrolyzate saccharides having a DE of from about 1.0 up to 100. The starch hydrolyzate sugars are reducing sugars which are readily converted to sugar esters in the anhydrous liquid system of the present invention. Other non-toxic sugars such as sucrose, fructose, or sugar substances such as the sugar alcohols, e.g. mannitol, may also be used to produce sugar esters for purification in accordance with the present invention.

The selected sugar is reacted with one or more organic acid chlorides or anhydrides thereof having at least 2 carbon atoms such as acetyl chloride and up to 22 or more carbon atoms. Acetyl chloride, lauroyl, palmitoyl and stearoyl chlorides have been used with excellent results. The amount of organic acid chloride used may vary but in general from about 0.1 mole to about 10.0 moles of organic acid chloride for each monosaccharide moiety is adequate. Preferably from about 1.0 to about 1.5 moles of sugar are used for each 1.0 mole of organic acid chloride. Increasing the amount of organic acid chloride above the stoichiometric amount of 1.0 mole of sugar to 1.0 mole of organic acid chloride will tend to produce sugar esters with higher degrees of substitution such as the di and tri, etc. esters of glucose.

The term organic acid chloride used in the description and claims includes one or more organic acid chlorides and anhydrides thereof having at least 2 carbon atoms and up to 22 carbon atoms and more.

One or more organic fatty acids having at least 2 carbon atoms and up to 22 and more carbon atoms, the anhydrides, esters and glyceride esters thereof as well as vegetable or animal fats or oils may be added to the reaction mixture in any desired amount. These fatty acid materials either alone or in combination have been found to react with the selected sugar in the presence of the selected organic acid chloride with advantage to produce mixed sugar esters. The amount of fatty acid materials will vary depending on the properties desired in the final sugar ester product, but in any event at least about 0.1 mole of the selected organic acid chloride for each mole of monosaccharide moiety will be employed in the reaction mixture to initiate reaction between the sugar and fatty acid material. The total amount of organic acid chloride and fatty acid material may be a maximum that will theoretically react with the sugar in the substantially anhydrous liquid reaction mixture. Other esters, alcohols (mono or polyhydric) and fatty acid materials may also be added to the reaction mixture as long as these do not exclude synthesis of sugar esters by the organic acid chloride.

The term fatty acid materials as used in the description and claims means one or more organic fatty acids having at least 2 carbon atoms, the anhydrides, esters and glyceride esters thereof and non-toxic vegetable or animal fats or oils containing glyceride esters.

Best results for the synthesis reaction in an anhydrous liquid system are achieved by subjecting the reaction atmosphere to a dry inert gas purge in known manner to strip moisture from the system. A dry nitrogen gas purge is conveniently used for this purpose. The dry inert gas purge is preferably initiated before reaction with the organic acid chloride and is continued throughout the synthesis reaction to maintain an anhydrous system for best results. While substantially anhydrous conditions for the synthesis reaction are most conveniently established with a dry gas purge, it will be understood that substantially anhydrous conditions may be established by any conventional means such as by using bone dry ingredients.

The substantially anhydrous synthesis reaction is preferably carried out by using a liquid solvent that will dissolve, suspend or hold the sugar in a colloidal dispersion to expedite contact of the reactants for transesterification preferably obtained by vigorous agitation or comparable means. Some solvents that may be used include acetic acid, glacial acetic acid, propionic acid and buteryic acid or any other non-toxic organic acid that is a liquid at the synthesis reaction temperature and which will dissolve, suspend or colloidally disperse the selected sugar for reaction with the organic acid chloride. The organic acid chlorides or the above-specified fatty acid material or mono or polyhydric alcohols such as glycerol may also be used as the solvent for the synthesis reaction.

Fatty acid material and the fatty acids are the preferred solvents which, as in the case of acetic acid, quite unexpectedly attach to the sugar molecule in the presence of the selected organic acid chloride to provide a mixed ester of superior emulsifying characteristics for use as an ingredient in food products. The organic acid chlorides having at least 2 carbon atoms and up to 22 carbon atoms and more may be used alone or in combination and may also be combined with one or more of the other solvents. The use of a combination of two different organic acid chlorides will produce mixed sugar esters, and mixed sugar esters are also achieved by combining an organic acid chloride with a fatty acid material. Acetic acid is one preferred fatty acid material and solvent which in the presence of an organic acid chloride having at least 3 carbon atoms will attach acetate groups to provide a mixed sugar ester. Use of an organic acid chloride alone as the reactant and solvent will produce a single ester of varying degrees of substitution depending on the amount of organic acid chloride used in the synthesis reaction.

The amount of solvent may be varied depending on the manufacturing equipment at hand but in general from about 1.0 ml to about 100.0 ml of solvent for each 0.001 mole of organic acid chloride has been found to be adequate.

The term solvent used in the description and claims means any substantially anhydrous material that is a liquid at the synthesis reaction temperature and pressure and will dissolve, suspend or hold sugar in a colloidal dispersion for synthesis reaction with the selected organic acid chloride.

It is of advantage for ease of synthesis reaction and high yield to employ a catalyst in the reaction mixture. The catalyst may be any of the mono or divalent basic salts of a weak acid. Suitable catalysts include potassium carbonate, potassium palmitate, potassium chromate and calcium propionate. The amount of catalyst may be varied and in general from about 0.01 mole to about 1.0 mole of catalyst may be used for each 1.0 mole of the organic acid chloride reactant. Preferably about 0.079 mole of catalyst is used for each 1.0 mole of organic acid chloride. Heat may also serve as catalyst for stimulating reaction. Reaction temperature may range from ordinary room temperature up to about 250° C. The preferred reaction temperature is from about 40° C. to about 100° C. In all cases the temperature is preferably maintained low enough to avoid caramelization of sugars which would give a product having poor emulsification characteristics and dark color.

In general it is of advantage to heat the solvent to from about 90° C. to about 116° C. to aid in suspending the selected sugar in the selected solvent. The selected reaction temperature is preferably below that which has an adverse effect on the organic acid chloride under the conditions of reaction. Adding a small amount of the palmitoyl chloride of up to 10% by weight of the total at about 90° C. will tend to keep the selected sugar in suspension when the reaction mixture is cooled down for reaction at about 45° C. to 55° C.

For best results of yield of product, an excess of sugar over the stoichiometric amount required for reaction with the organic acid chloride to produce the desired sugar ester is used in the reaction mixture. Another advantage of the purified esters synthesized from the anhydrous system in accordance with the present invention is the superior emulsifying characteristics of the sugar esters which makes them particularly attractive for use as an ingredient in food products.

The following examples of preferred embodiments illustrate further details and advantages of the present invention.

EXAMPLE I 50 ml of glacial acetic acid were heated in a four-necked flask fitted for heating, stirring, vacuum distillation and dry gas purge to 90° C. while subjected to a dry inert nitrogen gas purge to carry away moisture. 5.15 grams (0.015 mole) of maltose starch hydrolyzate sugar was added and mixed into the acetic acid solvent while the nitrogen gas purge was continued. The temperature was dropped to 70° C. whereupon about 10 ml of acetic acid were distilled off under a vacuum of 600 mm Hg in order to remove virtually all moisture and establish an anhydrous reaction mixture. The nitrogen purge was resumed after distillation and continued throughout the reaction along with continuous mixing of the ingredients.

The mixture was again heated to 90° C. to assist in suspending the sugar in the acetic acid and then about 0.1 ml of the organic acid chloride, palmitoyl chloride, was added and the mixture allowed to cool to 75° C. Potassium carbonate catalyst was added in the amount of 0.11 gram (.00079 mole) and when the mixture had cooled to about 70° C. the remainder of the palmitoyl chloride was slowly added dropwise. The total amount of palmitoyl chloride used in this example was 2.75 grams (0.01 mole). The temperature was allowed to drop to about 40° C. and the synthesis reaction was allowed to continue for 18 hours.

The resulting reaction mixture was transferred to a conventional rotary evaporator (10, FIG. 1) and as much as possible of the remaining acetic acid solvent was distilled off under vacuum. Thereafter 25 ml of a 15% aqueous solution of sodium chloride (14) was mixed with the residue and the water distilled off in the rotary evaporator (10). 25 ml of water (12) was added and distilled off. The process of adding water and distillation of the water was repeated three times until substantially all the acetic acid was removed from the reaction mixture. A final 25 ml of water was added to form an aqueous mixture for separation and extraction of the sugar esters. The aqueous mixture at room temperature was transferred to a conventional separation funnel (16) and 50 ml of diethyl ether was added and mixed with the aqueous mixture. Upon standing, three layers developed. The bottom mostly water layer was run off and collected (22). The middle layer of mixed water and ether was run off (20) into a distillation flask (34) and the top ether layer (18) was collected in a distillation flask (30). The same procedure was repeated two more times (22, 24) and then the bottom layer was placed in a conventional continuous extractor (40). In this example the middle layer (34) was added to the bottom water layer (40) and both were subjected to continuous extraction by flowing ether through the aqueous mixture to remove as much of the sugar esters as possible. The ether from the top layer and from the continuous extraction was distilled off (42, 30) to recover the separated and purified sugar esters. The yield of sugar esters having the highest degree of substitution from the top layer (32) was 3.90 grams and the yield of the middle range of substitution from 34 combined with the sugar esters with lowest degree of substitution (38) recovered at (44) was 1.75 grams for a total of 5.65 grams which was 97.25% of the theoretical stoichiometric yield of 5.81 grams of mono-ester.

It was determined that the sugar ester from the synthesis reaction had palmitate and acetate groups in various positions of substitution to provide a mixed sugar ester which could account for the unexpectedly high yield from the synthesis reaction.

The mixed sugar ester was of advantage since it had superior emulsifying characteristics as compared to the sugar esters of the prior art.

EXAMPLE II

In this example the procedure of Example I was repeated except that the middle portion taken off at 20 of FIG. 1 was not combined with the bottom water layer at 40 and the liquid was distilled off at 34 to recover mixed sugar esters having a middle range of substitution at 36.

The procedure and ingredients of the synthesis reaction of Example I was employed but in this Example, 20.636 grams of maltose starch hydrolyzate sugar were mixed into 200 ml of glacial acetic acid solvent and reacted with 11.026 grams of palmitoyl chloride in the presence of 0.45 gram of potassium carbonate catalyst. Reaction was continued for 50 hours and then the mixed sugar esters were recovered as stated above using the same amounts of salt solution and ether for extraction. The top layer yielded 13.738 grams of mixed sugar esters with the highest degree of substitution at 32 of FIG. 1. The middle layer yielded 1.032 grams of mixed sugar esters of middle range of substitution at 36 and the bottom water layer yielded 8.347 grams of mixed sugar esters with the lowest degree of substitution at 44. The combined yield of 23.117 grams was 99.47% of the stoichiometric yield of 23.24 grams. The mixed sugar esters having different degrees of substitution were recovered using the room temperature ether extraction procedure of Example I as described above in this Example II.

EXAMPLE III 50 ml of glacial acid solvent were heated in a closed system to 110° C. A dry nitrogen gas purge was used while 0.015 mole of maltose was added with vigorous agitation. 10 ml of the acetic acid solvent were distilled off under vacuum of 34 mm Hg. The nitrogen gas purge was interrupted during distillation and resumed during the remainder of the process. The reaction mixture was cooled to 70° C. whereupon 0.01 mole of palmitoyl chloride was added dropwise and mixed into the reaction mixture. The mixture was allowed to cool down to 30 to 40° C. and was held at this temperature with continued mixing for about 20 hours. The remaining acetic acid was distilled off in a rotary evaporator.

In this example the mixed sugar esters are mixed with 25 ml of water and continuous ether extraction is employed to recover the mixed sugar esters from the aqueous mixture at 16 of FIG. 1. The ether is distilled off to recover the mixed sugar esters as a dry white powder.

EXAMPLE IV

The procedure of Example I is repeated using the same amounts of ingredients except that glucose is used in place of maltose. A dry gas purge is used in place of the nitrogen gas purge and potassium palmitate is used as the catalyst in place of the potassium carbonate.

The mixed sugar esters are recovered using the same ether extraction procedure and ingredients of Example II to recover three portions of sugar esters each having different degrees of substitution.

EXAMPLE V

In this example 0.081 mole of lauroyl chloride is heated to 60° C. and held under a dry gas purge while 0.015 mole of glucose along with 0.08 mole of potassium carbonate are added with stirring. Reaction is allowed to continue for 15 hours with dry gas purge and stirring at reduced temperature of 40°–45° C. After reaction the unreacted lauroyl chloride is distilled off under vacuum and the laurate glucose sugar esters are recovered by forming an aqueous mixture which is subjected to continuous extraction at 16 with ethyl acetate which is distilled off to recover the sugar esters.

EXAMPLE VI 50 ml of glacial acetic acid were heated to 116° C. at which time 5.15 g (or approximately 0.015 mole) of 42 DE corn syrup solids were dissolved therein. A total of 0.01 mole of palmitoyl chloride was used for reaction. About 1.25 ml of the palmitoyl chloride were initially added and heating was discontinued. When temperature dropped to 100° C., 0.00079 mole of potassium carbonate was charged. At 95° C. the remaining 0.006 mole of palmitoyl chloride was slowly dropped into the vessel while the temperature dropped to 40°–50° C. over a period of 1–½ hours. The temperature was maintained at 40°–50° C. and reaction ran for 15 hours with a yield of 97% of mixed sugar esters.

The mixed sugar esters are purified and recovered after reaction using the same ingredients and ether extraction procedure set forth in Example II to recover three separate portions of sugar esters having different degrees of substitution.

EXAMPLE VII

The procedure of Example I was repeated using 50 ml glacial acetic acid, 0.015 mole maltose, 0.00079 mole potassium carbonate, 0.005 mole palmitoyl chloride and 0.005 mole of acetyl chloride.

The palmitoyl chloride was added to the sugar solution at 94° C. and the temperature was allowed to increase to 106° C. whereupon the acetyl chloride was slowly added and the temperature was allowed to drop to 80° C. and reaction was terminated. The mixed sugar ester was recovered after 35 minutes total reaction time.

Three separate portions of mixed sugar esters having different degrees of substitution were recovered using the ether extraction procedure and ingredients of Example II.

EXAMPLE VIII

In this Example 5.511 grams of maltose were dissolved in 50 ml of glacial acetic acid at 90° C. and held under a nitrogen gas purge while 2.754 grams of palmitoyl chloride followed by 0.11 gram of potassium carbonate was added with stirring. Temperature was allowed to drop to 45° C. while the palmitoyl chloride was being added. Reaction continued for 15 hours under the nitrogen gas purge at 45° C.

The raw sugar esters were recovered using the ingredients and ether extraction procedure described in Example I above except that the sugar esters were recovered separately from each of the top, middle and bottom layers. There were 3.468 grams of sugar esters of highest substitution recovered at 32 of FIG. 1. There were 1.133 grams of middle range of substitution sugar esters recovered at 36 and 1.158 grams of lowest substitution sugar esters were recovered at 44.

A mixture of acetone and methanol was poured over dry ice to form a freezing solution at the temperature of dry ice. Separate aqueous solutions of all three of the above sugar esters were formed by mixing each of them with 20 ml water in freeze drying flasks which were placed in the freezing solution to rapidly freeze the aqueous mixtures. The three separate aqueous frozen mixtures in the flasks were then subjected to a high vacuum to freeze dry the sugar esters in conventional manner. After eight hours the sugar esters in the containers were recovered as a light finely divided powder. There were 3.292 grams of the highest substituted sugar esters recovered. 1.046 grams of the middle substituted sugar esters and 1.035 grams of the lowest substituted sugar esters were recovered. The yield of freeze dried esters from the esters recovered from the system of FIG. 1 was 93.3%.

EXAMPLE IX 50 ml of glacial acetic acid were heated in a conventional reaction vessel to 110° C. A dry nitrogen gas purge was started and 5.136 grams of sucrose were added with vigorous agitation while the nitrogen gas purge was continued. After the sugar was suspended in the glacial acetic acid, 10.0 ml of acetic acid were distilled off under reduced pressure (300 mm HG vacuum). The nitrogen gas purge was discontinued during distillation. The reaction mixture was cooled down to about 86° C. whereupon 0.116 gram of potassium carbonate was added followed by 2.761 grams of palmitoyl chloride which were added dropwise to the reaction mixture while under nitrogen gas purge and vigorous agitation. The reaction mixture was allowed to cool to 40° to 50° C. and was held at this temperature for about 13 hours with continuous nitrogen gas purge and vigorous agitation.

After reaction, the remaining acetic acid was distilled off under vacuum in a rotary evaporator (10, FIG. 1). Thereafter 25 ml of a 15% aqueous solution of sodium chloride (14) were mixed with the residue and water was distilled off from the resulting aqueous mixture under vacuum in the rotary evaporator (10). This procedure of adding the salt solution and distilling off water was repeated three times to remove substantially all of the acetic acid solvent and thereafter 25 ml of water were added to form an aqueous mixture for extraction. The aqueous mixture was cooled to room temperature in a conventional separation funnel (16) and 50 ml of diethyl ether were added and mixed with the aqueous mixture. Upon standing, three layers formed in the separation funnel. The top mostly ether layer was removed at 18 and the bottom water layer was removed at 22. The middle ether and water emulsion layer was removed at 20 of FIG. 1.

A second extraction and a third extraction of the water layer was carried out at 22 and 24 respectively by mixing 50 ml of ether with the water layer at room temperature and the top separated ether layer was removed at 26 and 28 of FIG. 1. The remaining bottom water layer was subjected to continuous ether extraction at 40 until there was no sugar ester in the extraction ether. The top ether layers 18, 26 and 28 were combined at 30 and the ether from the continuous extraction was collected at 42. Ether was distilled off to recover the sugar esters with the highest degree of substitution at 32 and the sugar esters with the lowest degree of substitution were recovered at 44 by distilling off the ether. The liquid was vacuum distilled off the middle layer to recover the sugar esters with a middle range of substitution at 36.

Each of the three portions of mixed acetate and palmitate sugar esters recovered at 32, 36 and 44 were separately freeze dried for further purification using the same procedure described in Example VIII. The yield after freeze drying was 3.417 grams of sugar esters of highest degree of substitution. The yield of middle range of substitution was 0.267 gram and 1.007 grams of sugar ester with the lowest degree of substitution were recovered. The combined total yield was 80.7% of the theoretical yield.

EXAMPLE X

In this Example 50 ml of glacial acetic acid were heated to 95° C. and 5.15 grams of maltose were dissolved in the acetic acid under a nitrogen gas purge. The nitrogen gas purge was interrupted while 10 ml of acetic acid were distilled off at 85° C. under vacuum of 575 mm Hg. Thereafter the nitrogen gas purge was resumed and 0.135 gram of potassium carbonate was slowly added followed by the very slow addition of 0.785 gram of acetyl chloride. Reaction at about 70° C. under the nitrogen gas purge was continued for 33 hours. The acetic acid was distilled off to recover the acetate sugar esters.

After distilling off the acetic acid, the residue was purified using the ether extraction procedure and ingredients set forth in Example IX including the freeze drying purification step for each of the three separate portions of the mixed sugar esters.

EXAMPLE XI

The procedure of Example I was used for the synthesis reaction of maltose with palmitoyl chloride in the presence of glacial acetic acid and calcium propionate catalyst. 50 ml glacial acetic acid were heated to 94° C. and 5.161 grams of maltose were dissolved in the acetic acid under a nitrogen gas purge. The gas purge was interrupted while 10 ml of acetic acid were distilled off at 90° C. under a vacuum of 640 mm Hg. After distillation the nitrogen gas purge was resumed and 0.156 gram of calcium propionate catalyst was added followed by the slow addition of 2.832 grams of palmitoyl chloride. Reaction at 10° C. under the nitrogen gas purge was continued for 18 hours. The acetic acid was distilled off under vacuum. The yield of mixed sugar esters was 115% of the theoretical yield.

After distilling off the acetic acid, the residue was purified and the mixed sugar esters were separated using the ether extraction procedure and ingredients of Example IX except for the freeze drying step which was not used. 4.525 grams of mixed sugar esters having the highest degree of substitution were recovered at 32 of FIG. 1. The amount of sugar esters with the middle range of substitution recovered at 36 was 0.618 gram and 1.566 grams of the sugar esters with the lowest degree of substitution were recovered at 44 of FIG. 1. The yield of the total of sugar esters recovered was 115% of the theoretical yield.

EXAMPLE XII

The procedure of Example I was repeated using 50 ml glacial acetic acid, 5.152 grams of maltose, 0.156 gram of potassium chromate catalyst and 2.762 grams of palmitoyl chloride.

The maltose was added to the glacial acetic acid heated to a temperature of 90° C. and under a nitrogen gas purge. The gas purge was interrupted and 10 ml of acetic acid were distilled off under a vacuum off 675 mm Hg. After distillation the nitrogen gas purge was resumed and maintained throughout the reaction. The temperature of the mixture was maintained at 86°–90° C. while the potassium chromate catalyst was added followed by the slow addition of the palmitoyl chloride. Reaction was allowed to continue for 18 hours at 86°–90° C. The sugar esters were recovered by distilling off the acetic acid.

The residue that remained after distilling off acetic acid was purified and the mixed sugar esters were separated into three separate portions each having different degrees of substitution using the ether extraction procedure and ingredients of Example IX with the exception that the freeze drying step was not used.

EXAMPLE XIII

The procedure of Example XII is repeated with the same ingredients except that acetone is used in place of ether in the room temperature extraction of three separate portions of sugar esters each having different degrees of substitution.

EXAMPLE XIV

The emulsifying characteristics of the sugar esters of the present invention were compared to prior art sugar esters. Cakes were prepared and baked using the standard procedure of the American Association of Cereal Chemists (AACC).

White cakes were prepared and baked in accordance with the standard AACC procedure as follows:
Baking
Use 6 inch cake pans
Heat oven to 375° F., bake cakes for 19 minutes, cool 30 minutes, remove from pan and cool 30 minutes, measure.
Batter Mix

| | |
|---|---|
| Cake flour at 14% moisture | 111.28 g |
| Extra-fine granulated sugar | 155.79 g |
| Shortening | 55.64 g |
| Nonfat dry milk | 13.35 g |
| Salt | 3.34 g |
| Baking powder | 5.84 g |
| Egg white | 10.02 g |
| Distilled water | 144.66 g |

Grease and line baking pans with waxed paper. Sift dry ingredients twice.
1. Cream shortening and creamy emulsifier (if used) for 1 minute at speed 6 on a Hobart K5a mixer.
2. Scrape down bowl. Add dry ingredients and all but 60 ml of $H_2O$. Mix 30 seconds on low speed.
3. Scrape bowl and beaters. Mix 4 minutes at speed 6.
4. Scrape. Add 30 ml of water. Mix 30 seconds at low speed.
5. Scrape. Mix 2 minutes at speed 6.
6. Scrape. Add 30 ml of water. Mix 30 seconds at low speed.
7. Scrape. Mix 2 minutes at speed 6.
8. Tare pan and add about 235 g of batter.
To adjust flour to 14% mwb: amount of flour used = X $$(111.28 \text{ g})(0.86) = \frac{(100 - \% \text{ moisture})}{100} X$$

Measure diameter of cake (measured 1 cm from bottom). Measure height of cake using the template.

$$\text{Volume (cm}^3\text{)} = \frac{D^2 \cdot \pi \cdot (B + C + D)}{12}$$

Four cakes of equal weight using the batter and procedure specified above were prepared and baked. The batter of cake A contained 1.0% and cake B batter contained 2.0% of the sugar esters produced in accordance with Example I hereinabove of the present invention. The batter of cake C contained 1.0% and the batter of cake D contained 2.0% of the sugar esters supplied by Dai-Ichi Kogyo Seiyaku Co. Ltd. and described in U.S. Pat. No. 3,748,324.

In each case the percent by weight of sugar ester was based on the weight of cake flour used in the batter mix and the weight of added sugar ester was subtracted from the weight of cake flour used to prepare the batter. Both sugar esters were of a comparable low degree of substitution.

The volume of the baked cakes were measured in accordance with the AACC specification.

The volume of cake A was 600 $cm^3$ while the volume of cake C containing the prior art sugar ester was only 555 $cm^3$. The volume of cake B was 605 $cm^3$ while the volume of cake D was only 520 $cm^3$. The texture of the batters of cakes A and B were observed to be smooth and creamy while the texture of the batters of cakes C and D were definitely rough and curdled. The crumbs of cakes A and B were finer and more uniform inside than cakes C and D.

EXAMPLE XV

In this Example 1.0% of the sugar esters produced in accordance with Example II hereinabove were used in the batter of cake E instead of the sugar esters of Example I and 1.0% of the sugar esters of U.S. Pat. No. 3,748,324 supplied by Dai-Ichi Kogyo Seiyaku Co. Ltd. were used in the batter of cake F. Otherwise, the ingredients, amount of ingredients and the mixing of batter and baking procedure of the AACC set forth in Example XIV were used in baking the cakes E and F in this Example XV. The cake volumes measured by the AACC procedure were: Cake E volume was 520 cm$^3$ and cake F volume was 490 cm$^3$. The texture of the batter of cake E was smooth and only slightly curdled while the texture of the batter of cake F was rough and very definitely curdled.

EXAMPLES XVI-XVIII

These examples illustrate the use of the present purification process on raw sugar esters made in an aqueous environment. The amounts of each addition are shown in table form below which is preceded by a general description of the method employed. It is readily apparent by comparing the following description with that in Example I above that the steps are virtually identical.

First, a 15% aqueous salt solution of sodium chloride was mixed with the raw sugar esters (FIGS. 1, 10 and 14). Then water was added to dilute the mixture (12). This mixing was carried out at both room temperature and pressure. After mixing, the aqueous mixture at room temperature was transferred to a conventional separation funnel (16) and an amount of diethyl ether was added and mixed with the aqueous mixture. Upon standing at room temperature, three layers developed. The bottom mostly water layer was run off and collected (22). The middle layer of mixed water and ether was run off (20) into a distillation flask (34) and the top ether layer (18) was collected in a distillation flask (30). The same procedure was repeated two more times (22, 24) and then the bottom layer was placed in a conventional continuous extractor (40). In this example the middle layer (34) was added to the bottom water layer (40) and both were subjected to continuous extraction by flowing ether through the aqueous mixture to remove as much of the sugar esters as possible. The ether from the top layer and from the continuous extraction was distilled off (42, 30) to recover the separated and purified sugar esters. The yields of each layer of sugar esters are also shown below. The yields are illustrated as weight percentages of the total weight of raw sugar esters present prior to the purification process.

|  | EXAMPLE XVI | EXAMPLE XVII | EXAMPLE XVIII |
| --- | --- | --- | --- |
| 15% NaCl aq. (ml) | 50 | 25 | 25 |
| Water (ml) | — | — | — |
| Ether (ml) (three times) | 50 | 50 | 50 |
| Top Layer - Yield | 14.8% | 10.1% | 25.3% |
| Middle Layer - Yield | 57.7% | 32.4% | 53.5% |
| Bottom Layer - Yield | 12.5% | 0.5% | 1.0% |
| Total - Yield | 85.0% | 43.0% | 79.8% |
| pH before purification | about 9 | about 9 | about 9 |
| pH after purification | about 9 | about 9 | about 9 |

EXAMPLE XIX

This example illustrates the use of sugar esters purified in Examples XVI-XVIII for making cakes. Following the procedures in Example XIV, cakes were made, each containing 0.5% sugar esters, and each was a satisfactory cake.

EXAMPLE XX

This example illustrates the further purification of the top layer of the three-layer system as disclosed in FIG. 2.

Following the procedure in Example I, the top layer was pulled off and distilled at 40° C. under vacuum at 34 mm Hg. There was 6.33 grams of material which was added to 50 ml of water. This mixture was heated to between 85° C. and 90° C. with constant stirring. Once the mixture obtained 85° C. to 95° C., 2.45 grams of calcium carbonate (CaC0$_3$) was added and mixed. The fatty acid used to prepare the raw sugar ester was palmitic acid with a molecular weight of about 258.43 grams. The mixture was then removed from the heat and allowed to cool. During both heating and cooling, the mixture was constantly stirred.

The mixture was then filtered through a Buchner Funnel with No. 2 Whatman paper and the filtrate distilled to obtain the sugar ester. This filtering process was carried out two more times using the precipitate from the previous filtration.

The final precipitate was then crushed, mixed with 100 ml of water and 35 ml of 1 N hydrochloric acid, heated to 100° C. and then cooled to room temperature with constant stirring. This mixture was filtered and the filtrate discarded. The precipitate was saved and mixed with 50 ml of water and 50 ml of ether and was transferred to a separatory funnel and allowed to stand. Upon standing, three layers formed. The bottom two layers were recovered and distilled for sugar ester while the top layer was discarded.

The total amount of sugar ester obtained from this process was 1.857 grams. The amount of sugar ester obtained from the other two layers with the rest of the purification process was 4.852 grams; thus, a total of 6.709 grams of sugar ester was obtained. The theoretical amount of sugar ester to be obtained from overall purification was 9.64 grams; therefore, a percentage yield from the present invention with this additional purification step of the top layer is about 70%.

EXAMPLE XXI

This is another example which illustrates the further purification of the top layer to obtain a higher percentage yield, as disclosed in FIG. 2.

After distillation, 7.465 grams of solid material was left. This was mixed with 50 ml of water and heated to 95° C. with constant stirring. 2.89 grams of calcium carbonate was added and the mixture was then cooled to room temperature while the mixture was constantly stirred. The raw sugar ester was made from palmitic acid. The mixture was then filtered through a Buchner funnel with No. 4 Whatman paper. The filtrate was collected, distilled and dried to obtain sugar esters.

The precipitate was then mixed with 50 ml of water and refiltered. Then the filtrate was distilled to obtain sugar esters while the precipitate was added to water and refiltered. The filtrate again was collected and distilled to obtain sugar esters.

The final precipitate was then added to 100 ml of water and 35 ml of 1 N hydrochloric acid, heated to between 85° C. and 95° C. and allowed to cool to room temperature with constant stirring. This was filtered, the filtrate discarded and the precipitate crushed and mixed with 50 ml of water. This new mixture was refiltered and the filtrate was discarded; it contained mostly salts. The precipitate from this filtration was then mixed with 50 ml of ether and 50 ml of water and placed in a separatory funnel. Upon standing, three layers were formed. The top layer was discarded and the bottom two were distilled to obtain sugar esters.

77% of the theoretical yield was obtained.

The sugar esters of the present invention are shown by actual comparison tests to be superior to prior art sugar esters and the yields of sugar esters produced in accordance with the present invention were unexpectedly high as compared to prior art processes.

EXAMPLE XXII

In this example the procedure of Example I was repeated except that water at (29) was added to the top layer (28) prior to distillation at (30). The solution from the distillation step 30 was dried and a sugar ester obtained.

EXAMPLE XXIII

In this example the procedure of Example XX was followed except that after the top layer (28) was pulled off, water (29) was added prior to the distillation step 50. Step 52 was not needed because water was present. The remaining purification process was followed.

EXAMPLE XXIV

In this example the procedure of Example I was followed except that water was added at (29) and instead of distilling at (30), the solution was added to a separation funnel where the water layer was extracted and the ether layer remained. After this first extraction step, more ether was added to the water layer and the extraction was repeated. Thus, the addition of ether and extraction of the water was repeated two times. The aqueous solution was then dried and a sugar ester obtained.

EXAMPLE XXV

In this example the procedure of Example I was followed except that water was added at (29) prior to the distillation at (30). After the distillation at (30), an aqueous solution remained and ether was added to the aqueous solution. The aqueous-ether solution was then redistilled to boil off the ether. Again, an aqueous solution remained to which ether was added and a distillation step was performed. Thus, the addition of ether and distillation step was carried out two times. The final aqueous solution was dried and a sugar ester obtained.

It will be understood that it is intended to cover all changes and modifications of the preferred embodiments of the invention herein chosen for the purpose of illustration which do not constitute a departure from the spirit and scope of the invention.

What is claimed is:

1. A method for separating and purifying raw sugar esters from a mixture which comprises the steps of mixing the raw sugar esters with an aqueous salt solution, adding an organic extraction solvent to said aqueous mixture, mixing said extraction solvent with said sugar esters in said aqueous mixture whereby three layers are formed, separating said extraction solvent from said aqueous mixture and separating the purified sugar esters from said extraction solvent.

2. In the method of synthesizing sugar esters in a substantially anhydrous liquid system by reacting one or more starch hydrolyzate sugars with an organic acid chloride having at least two carbon atoms to esterify the hydrolyzate sugar and form sugar esters, the improvement which comprises the steps of adding an aqueous salt solution to said sugar esters to form an aqueous mixture, removing water from said aqueous mixture, adding an organic extraction solvent to said aqueous mixture, mixing said extraction solvent with said sugar esters whereby three layers form, separating the extraction solvent from said aqueous mixture and recovering said sugar esters from the extraction solvent by distilling off the solvent.

3. A method for separating and purifying raw starch hydrolyzate sugar esters which comprises the steps of forming an aqueous mixture of the raw sugar esters and a salt, contacting the sugar esters in said aqueous mixture with an organic extraction solvent whereby three layers form, removing the solvent from the aqueous mixture and separating the esters from the solvent to recover the purified sugar esters.

4. A method of separating and purifying raw sugar esters from a mixture which comprises:
   (a) mixing the raw sugar ester with an aqueous salt solution;
   (b) adding an organic extraction solvent to said aqueous mixture;
   (c) mixing said organic extraction solvent into said aqueous mixture;
   (d) allowing the aqueous mixture of organic extraction solvent, salt solution and raw sugar ester to stand whereby three layers are formed;
   (e) separating said extraction solvent from said aqueous mixture; and
   (f) separating and purifying said sugar esters from said extraction solvent.

5. The method of synthesizing starch hydrolyzate sugar esters in a substantially anhydrous liquid system by reacting one or more starch hydrolyzate sugars with an organic acid chloride having from 2 to about 22 carbon atoms to esterify the hydrolyzate sugar and form sugar esters, adding an aqueous salt solution to the sugar esters to form an aqueous mixture, mixing an organic extraction solvent with said aqueous mixture whereby three layers form, separating organic solvent containing sugar esters from said aqueous mixture and separating sugar esters from the separated organic extraction solvent.

6. The method of claim 5 which includes the step of adding a second portion of organic extraction solvent to said aqueous mixture that remains after the first extraction, separating the second portion of organic extraction solvent containing sugar esters from said aqueous mixture and separating a second portion of sugar esters from said second step organic extraction solvent having a degree of substitution different from said first separated sugar esters.

7. The method of claim 5 in which the one or more starch hydrolyzate sugars are reacted with said organic acid chloride in the presence of a fatty acid material to form mixed sugar esters.

8. The method of claim 7 in which the selected organic acid chloride is palmitoyl chloride and the selected fatty acid material is glacial acetic acid and in which the sugar esters are a mixed palimate and acetate ester.

9. The method of claim 7 in which the selected organic acid chloride is acetyl chloride or palmitoyl chloride.

10. The method of claim 5 which includes the step of synthesizing the sugar esters in a non-toxic substantially anhydrous solvent.

11. The method of claim 10 in which the solvent is palmitoyl chloride or acetyl chloride.

12. The method of claim 5 which includes the step of carrying out the synthesis reaction at a temperature of about 30° C. to 45° C.

13. The method of claim 5 which includes the step of carrying out the synthesis reaction in the presence of a catalyst which stimulates reaction.

14. The method of claim 13 in which the catalyst is potassium palmitate or potassium carbonate.

15. The method of claim 5 in which the starch hydrolyzate sugar is maltose or glucose.

16. The method of producing, purifying and separating sugar esters which comprises the steps of reacting under substantially anhydrous conditions one or more sugars with an organic acid chloride having at least two carbon atoms to form said sugar esters, adding an aqueous salt solution to said sugar esters to form an aqueous mixture, removing water from said aqueous mixture, adding an organic extraction solvent to said aqueous mixture whereby three layers form, separating the organic extraction solvent aqueous mixture into at least three separate portions containing sugar esters and separating the sugar esters.

17. The method of claim 16 in which the sugar esters separated from each of the separate portions have different degrees of substitution.

18. The method of claim 16 in which the aqueous mixture is formed by mixing the sugar esters with water and by adding salt to said aqueous mixture.

19. The method of claim 16 which includes the steps of reacting the organic acid chloride with the one or more sugars in a solvent mixture and heating the aqueous mixture after reaction to distill off solvent before adding the organic extraction solvent to the remaining aqueous mixture.

20. The method of claim 19 in which the selected solvent for the synthesis reaction with the organic acid chloride is acetic acid.

21. The method of claim 16 which includes the steps of separating the aqueous organic extraction solvent mixture into a first portion containing the major portion of solvent, and into a second separate portion of mixed solvent and water and into a third separate portion which contains the major portion of the water, adding additional organic extraction solvent to said third portion, separating said organic extraction solvent from said third portion and separating sugar esters from said additional organic solvent, separating sugar esters from said first and said second portions to recover three portions of sugar esters each of which have different degrees of substitution.

22. The method of claim 21 which includes the steps of combining the first and second portions of said aqueous organic extraction solvent mixture and thereafter separating sugar esters from the combination of said first and second portions.

23. The method of claim 22 which includes the steps of combining the second and third portions of said aqueous organic extraction solvent mixture, adding additional organic extraction solvent to the combination of said second and third portions, separating the added organic solvent and separating sugar esters from said added organic solvent.

24. The method of producing sugar esters which comprises the steps of reacting under substantially anhydrous conditions one or more sugars with an organic acid chloride having from 2 to about 22 carbon atoms in the presence of a catalyst to form sugar esters, forming an aqueous mixture containing salt and said sugar esters, adding an organic extraction solvent to said aqueous mixture whereby three layers form, separating said aqueous organic solvent mixture into a first portion containing a major portion of organic extraction solvent said first portion containing one of said three layers and a second portion containing a major portion of water said second portion containing two of said three layers, recovering sugar esters from said second portion and recovering sugar esters from said first portion having a different degree of substitution from the sugar esters recovered from said second portion.

25. The method of claim 24 which includes the step of adding a fatty acid material to the synthesis reaction to form mixed sugar esters.

26. The method of claim 24 in which the organic extraction solvent is ether.

27. The method of claim 1 which includes the step of mixing said separated sugar esters with water and freeze drying the resulting aqueous mixture.

28. The method of producing and purifying sugar esters which comprises the steps of reacting one or more sugars with an organic acid chloride under substantially anhydrous conditions to produce sugar esters, and purifying said sugar esters by forming an aqueous mixture from which the sugar esters are extracted by means of an organic extraction solvent whereby three layers form prior to extraction.

29. The method of claim 28 which includes the step of further purifying said sugar esters by freeze drying.

30. A method of separating sugar esters into groups according to their degree of substitution comprising the steps of mixing the sugar esters with an aqueous salt solution, adding an organic extraction solvent to said aqueous mixture, mixing said extraction solvent with said sugar esters in said aqueous mixture, forming three layers and separating from one said layer sugar esters with different degrees of substitution than sugar esters separated from the other layers.

31. A method for separating and purifying raw sugar esters from a mixture which comprises the steps of:
 (a) mixing raw sugar esters with an aqueous salt solution to form a first aqueous mixture;
 (b) adding an organic extraction solvent to said first aqueous mixture;
 (c) mixing said extraction solvent with said sugar esters in said first aqueous mixture whereby three layers are formed;
 (d) separating the top layer of said layers from the other layers;
 (e) precipitating a first precipitate from said top layer;
 (f) mixing said precipitate with water to form a second aqueous mixture;
 (g) heating said second aqueous mixture;
 (h) adding a salt to said second aqueous mixture;
 (i) cooling and filtering said second aqueous mixture to obtain a second precipitate;
 (j) separating purified sugar esters from the filtrate obtained in step (i) above;
 (k) crushing said second precipitate and adding water and an acid to said second crushed precipitate to form a third aqueous mixture;
 (l) heating and cooling said third aqueous mixture;
 (m) precipitating out a third precipitate;
 (n) adding and mixing in an organic extraction solvent whereby at least two distinct layers are formed;
 (o) separating pure sugar esters from the bottom two said layers formed in steps (c) and (n) above.

* * * * *